US007967766B2

(12) United States Patent
Ravikumar

(10) Patent No.: US 7,967,766 B2

(45) Date of Patent: Jun. 28, 2011

(54) COMPRESSION GARMENT WITH HEEL ELEVATION

(76) Inventor: Sundaram Ravikumar, Briarcliff Manor, NY (US)

( * ) Notice: Subject to any disclaimer, the term of this patent is extended or adjusted under 35 U.S.C. 154(b) by 0 days.

(21) Appl. No.: 11/494,720

(22) Filed: Jul. 27, 2006

(65) Prior Publication Data

US 2007/0161933 A1 Jul. 12, 2007

Related U.S. Application Data

(63) Continuation-in-part of application No. 11/356,692, filed on Feb. 17, 2006, now Pat. No. 7,909,787.

(60) Provisional application No. 60/730,766, filed on Oct. 27, 2005.

(51) Int. Cl.
*A61F 5/00* (2006.01)

(52) U.S. Cl. ............................................ 602/13; 602/23

(58) Field of Classification Search ................ 602/5, 16, 602/23, 27, 28–29, 13; 128/846, 882
See application file for complete search history.

(56) References Cited

U.S. PATENT DOCUMENTS

| | | | | |
|---|---|---|---|---|
| 3,939,829 A | | 2/1976 | Spann | |
| 3,946,451 A | | 3/1976 | Spann | |
| 4,013,069 A | | 3/1977 | Hasty | |
| 4,030,488 A | | 6/1977 | Hasty | |
| 4,054,129 A | * | 10/1977 | Byars et al. | 601/152 |
| 4,186,738 A | | 2/1980 | Schleicher | |
| 4,197,845 A | | 4/1980 | Browning | |
| 4,266,298 A | * | 5/1981 | Graziano | 2/22 |
| 4,320,746 A | | 3/1982 | Arkans | |
| 4,399,815 A | | 8/1983 | Bachorik | |
| 4,402,312 A | | 9/1983 | Villari | |
| 4,409,975 A | | 10/1983 | Simhoni | |
| 4,730,610 A | | 3/1988 | Graebe | |
| 4,944,060 A | | 7/1990 | Peery | |
| 5,085,214 A | | 2/1992 | Barrett | |
| 5,226,245 A | | 7/1993 | Lamont | |
| 5,328,445 A | | 7/1994 | Spahn | |
| 5,412,822 A | | 5/1995 | Kelly | |
| 5,431,624 A | | 7/1995 | Saxton | |
| 5,435,009 A | | 7/1995 | Schild | |
| 5,449,339 A | | 9/1995 | Drennan | |
| 5,476,105 A | | 12/1995 | Toth | |
| 5,489,259 A | | 2/1996 | Jacobs | |
| 5,666,681 A | | 9/1997 | Meyer | |
| 5,711,760 A | | 1/1998 | Ibrahim | |
| 5,765,564 A | | 6/1998 | Ewing | |
| 5,839,139 A | | 11/1998 | Fink | |
| 5,876,364 A | | 3/1999 | Herbst | |
| 5,913,841 A | | 6/1999 | Lamont | |
| 5,957,872 A | | 9/1999 | Flick | |
| 5,957,874 A | | 9/1999 | Klein | |
| 5,997,491 A | | 12/1999 | Harris | |
| 6,001,119 A | | 12/1999 | Hampson | |
| 6,149,613 A | | 11/2000 | Klein | |
| 6,151,739 A | | 11/2000 | Meyer | |

(Continued)

*Primary Examiner* — Michael A. Brown

(74) *Attorney, Agent, or Firm* — Scott D. Wofsy; Edwards Angell Palmer & Dodge LLP

(57) ABSTRACT

A garment that includes at least one inflatable chamber for applying compression to a limb for assisting venous return, and an elevation member to elevate the limb. The elevation member may comprise an inflatable chamber, and the garment may be configured for compressive therapy of the leg while elevating the heel, eliminating or otherwise reducing or mitigating pressure on an individual's heel while the leg is in an extended position and undergoing compressive therapy.

16 Claims, 8 Drawing Sheets

U.S. PATENT DOCUMENTS

| | | | | |
|---|---|---|---|---|
| 6,175,979 | B1 | 1/2001 | Jackson | |
| 6,260,221 | B1 | 7/2001 | Grabell | |
| 6,290,662 | B1 | 9/2001 | Morris | |
| 6,351,863 | B1 | 3/2002 | Meyer | |
| 6,494,852 | B1 | 12/2002 | Barak | |
| 6,572,573 | B1 * | 6/2003 | Klein | 602/23 |
| 6,634,045 | B1 | 10/2003 | DuDonis | |
| 6,786,879 | B1 | 9/2004 | Bolam | |
| 6,789,284 | B2 | 9/2004 | Kemp | |
| 6,877,178 | B2 | 4/2005 | Chapman | |
| 2001/0016960 | A1 | 8/2001 | Grabell | |
| 2002/0032485 | A1 | 3/2002 | Flam | |
| 2003/0028135 | A1 * | 2/2003 | Flick et al. | 602/13 |
| 2003/0182727 | A1 | 10/2003 | DuDonis | |
| 2005/0060808 | A1 | 3/2005 | Shaw | |
| 2005/0070828 | A1 | 3/2005 | Hampson | |
| 2005/0107728 | A1 | 5/2005 | Vetters | |
| 2005/0222526 | A1 | 10/2005 | Perry | |

* cited by examiner

COMPRESSION GARMENT WITH HEEL ELEVATION

CROSS REFERENCE TO RELATED APPLICATIONS

This application is a continuation-in-part of application Ser. No. 11/356,692, filed Feb. 17, 2006, now U.S. Pat. No. 7,909,787 which claims the benefit of provisional Application No. 60/730,766, filed Oct. 27, 2005, each of which is hereby incorporated by reference in their entirety.

BACKGROUND OF THE INVENTION

1. Field of the Invention

The present invention relates generally to compression systems for vascular therapy and, more particularly, to a compression garment that stimulates or assists venous and/or arterial blood flow and also prevents, treats, and/or relieves decubitus ulcers.

2. Background Information

Various conventional compression devices are known for applying intermittent compressive pressure to a patient's limb. Such devices employ a garment (e.g., a sleeve) having one or more inflatable chambers, with the garment configured to be disposed about a patient's limb (e.g., leg and/or foot) such that intermittent inflation of the chamber(s) causes increased pressure to be applied intermittently against the patient's limb, causing increased blood flow velocity, assisting venous return. In some of these devices, referred to as sequential compression devices, multiple (i.e., two or more) chambers disposed along the venous path are controllably inflated sequentially.

These types of devices are used to assist in a large number of medical indications, mainly for preventing deep vein thrombosis (DVT) or other vascular disorders, reducing the occurrence of edemas, and facilitating wound healing. For instance, persons subject to extended periods of bed rest or inactivity (e.g., post-operative recovery) are often susceptible to DVT, which is a clotting of venous blood in the lower extremities and/or pelvis. This clotting occurs due to the absence of muscular activity in the lower extremities required to pump the venous blood (stasis). Such clotting may also occur due to a local vascular injury or a hypercoaguble state. The condition can be life-threatening if a blood clot migrates to the lung, resulting in a pulmonary embolus or otherwise interfering with cardiovascular circulation.

Typically, the compression devices are applied to the leg and/or foot when the patient is in the operating room or in the bed, and left in place until the patient ambulates fully or until the time of discharge. The hospitalized patients, when in bed for a prolonged period of time, have a tendency to form pressure ulcers. In many cases, the patient may already be predisposed to ulcer formation because of, for example, reduced circulation. One of the places where the pressure ulcer develops is the heel. More specifically, because of its thin layer of subcutaneous tissue between the skin and bone, the heel is the second most common site for pressure ulcer development (after the sacrum). Heel ulcers are costly and, if not treated promptly and properly, may lead to osteomyelitis and even limb amputation. Compressive therapy devices do not include means for preventing heel ulcer formation and thus, individuals receiving compressive therapy to treat any of a variety of indications are put at risk of developing heel ulcers.

SUMMARY OF THE INVENTION

Various embodiments of the present invention provide such advancements and overcome the above mentioned and other problems and limitations of the background art, by providing a method and apparatus for eliminating or otherwise reducing or mitigating pressure on an individual's heel while the leg is receiving compressive therapy.

In accordance with an aspect of the present invention, a compression garment comprises a backing member configured to be disposed about at least a lower leg portion of an individual between the calf and heel region, the backing member having an inner surface to be disposed facing the leg, and having an opposite outer surface; at least one compression bladder disposed on the inner surface of the backing member; and an elevation member mechanically coupled to said backing member and configured such that when the backing member is disposed about at least the lower leg portion of the individual the elevation member is capable of elevating the heel from an underlying surface in the event that the lower leg portion is extended above the underlying surface.

The elevation member may comprise an inflatable bladder, which, in some implementations is pneumatically independent from each of the at least one compression bladder and, in some implementations is pneumatically coupled to at least one of said at least one compression bladder. The inflatable bladder may be disposed on the outer surface of said backing member, and may be deflatable.

In accordance with another aspect of the present invention, a compression garment comprises at least one compression chamber capable of being coupled to a fluid source and configured to inflate and apply pressure against at least a portion of an individual's limb in response to receiving a fluid input from the fluid source; and at least one inflatable elevation chamber configured to elevate at least a portion of the individual's limb when inflated. In some implementations, the individual's limb is a leg and the at least one inflatable elevation chamber is configured to elevate the individual's heel.

In accordance with yet another aspect of the present invention, a compression garment comprises means for applying compressive pressure against at least a portion of an individual's lower leg by expanding in response to receiving a fluid input; and means for elevating the individual's heel from an underlying surface in the event that the lower leg is rested on the underlying surface, wherein the elevating means and applying means are integrally coupled mechanically. In some implementations, the elevating means comprises at least one inflatable elevation chamber, and the applying means comprises at least one inflatable compression chamber. In some implementations, the elevating means is implemented as at least one of a fluid filled member that is not adapted for deflation, and a preformed non-fluid filled cushion member that is not adapted for deflation.

It will be appreciated by those skilled in the art that the foregoing brief description and the following detailed description are exemplary and explanatory of this invention, but are not intended to be restrictive thereof or limiting of the advantages which can be achieved by this invention. Additionally, it is understood that the foregoing summary of the invention is representative of some embodiments of the invention, and is neither representative nor inclusive of all subject matter and embodiments within the scope of the present invention. Thus, the accompanying drawings, referred to herein and constituting a part hereof, illustrate embodiments of this invention, and, together with the detailed description, serve to explain principles of this invention.

BRIEF DESCRIPTION OF THE DRAWINGS

Additional aspects, features, and advantages of embodiments of the invention, both as to structure and operation, will be understood and will become more readily apparent when the invention is considered in the light of the following description made in conjunction with the accompanying drawings, in which like reference numerals designate the same or similar parts throughout the various figures, and wherein.

DETAILED DESCRIPTION OF EMBODIMENTS OF THE INVENTION

Figure 1A:
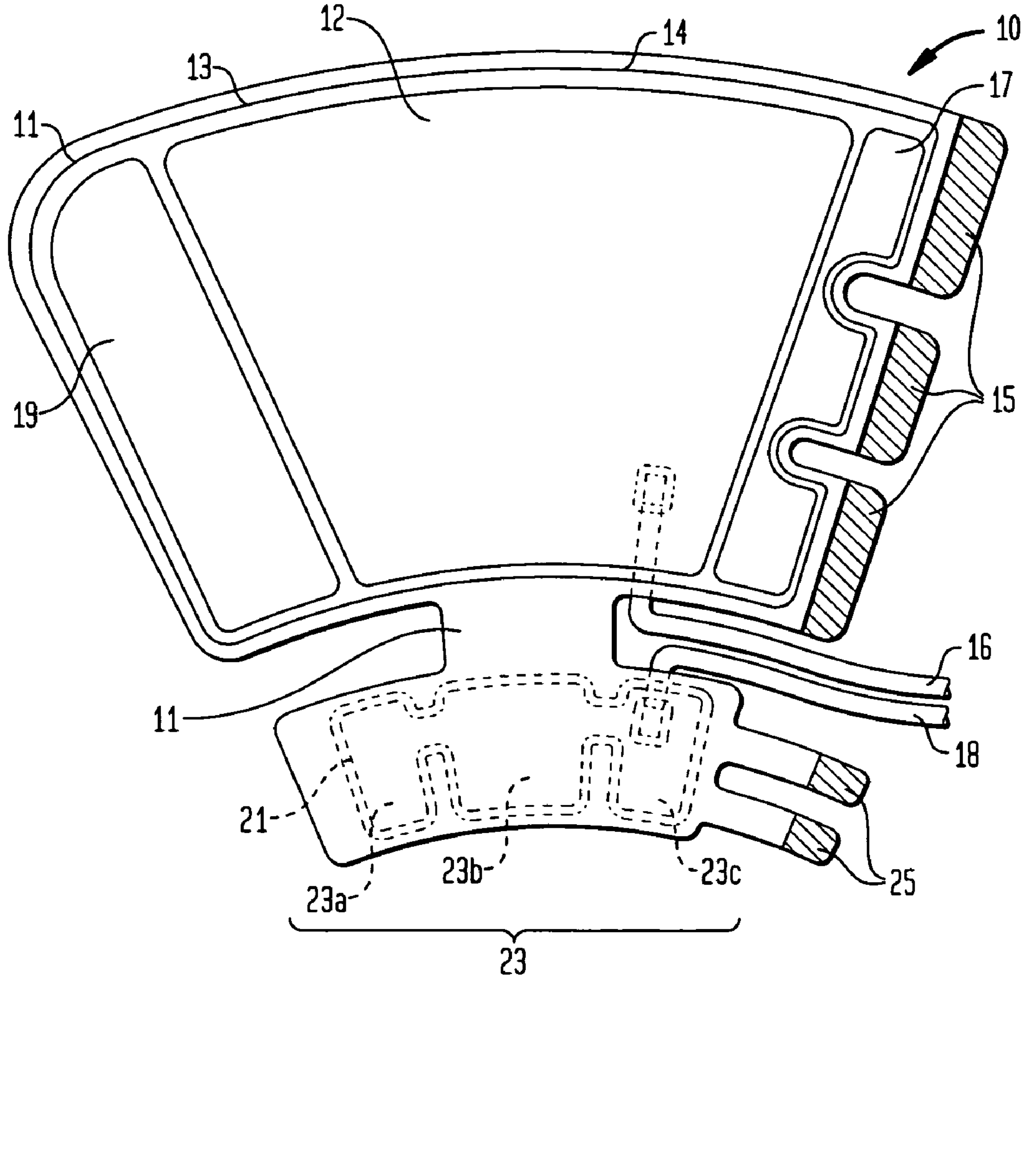
FIGS. 1A and 1B illustrate plan views of a compression garment, in accordance with an embodiment of the present invention.

As will be understood and more fully appreciated from the ensuing description, embodiments of the present invention are configured for attachment to the leg and/or foot to provide for compression therapy while also reducing or eliminating pressure on the heel region of the foot when the leg or foot is positioned such that the heel is in contact with an underlying surface (e.g., a bed) or would be in contact with an underlying surface but for the presence of the device. That is, as will be further understood below, while embodiments of the present invention may be implemented to sufficiently elevate the foot to provide for spatial separation of the heel from an underlying surface that the heel would otherwise rest upon, such and other embodiments of the present invention need not be used to provide such spatial separation of the heel, but rather may be advantageously used to reduce pressure on the heel even if the heel is in contact with an underlying surface. Additionally, even when the foot may be cantilevered over the end of a bed or other supporting structure, embodiments of the present invention may be used to provide cantilever elevation and support, and to prevent or otherwise reduce pressure on the heel region as the individual moves while the heel is originally in a cantilevered position.

As also will be understood in view of the ensuing description, embodiments of a compression treatment system and methods of operation are discussed in terms of vascular therapy including a prophylaxis compression apparatus for application to a limb of a body and, more particularly, in terms of a compression treatment system having a controller that is adaptable for inflating thigh, calf, ankle and/or foot sleeves, and may also be configured for inflating one or more inflatable heel elevation bladders. In particular, a compression treatment system in accordance with various embodiments of the present invention includes a controller, interconnecting tubing, and at least one inflatable garment. The controller may include a pressure transducer, a manifold, and at least one output port adapted for fluidly coupling the controller to the at least one inflatable garment using interconnecting tubing. The at least one inflatable garment includes at least one inflatable bladder for providing compressive therapy to a patient's leg (e.g., thigh, calf, or ankle, or any combination thereof), and also includes at least one support member, which may include at least one inflatable bladder, for elevating the patient's heel. It is contemplated that a compression treatment system according to various embodiments of the present invention may be employed for preventing, alleviating, and/or treating conditions arising from patient immobility, such as DVT, peripheral edema, decubitus ulcers, etc. It is contemplated that embodiments of compression treatment systems according to the present invention are not limited to any particular compression chamber configuration or pumping sequence, and include and are applicable to, for example, single chamber intermittent compression garments, as well as multi-chamber sequential compression garments. As used herein, intermittent compression garments or devices include sequential compression garments or devices; said differently, a sequential compression garment or device is a particular type of intermittent compression garment or device.

In the discussion that follows, the term "proximal" refers to a portion of a structure that is closer to a torso of a subject and the term "distal" refers to a portion that is further from the torso. Additionally, as used herein, the term "garment" is a generic term that includes, for example, foot cuff, knee sleeve, or leg sleeve, and is neither indicative of nor limited to any particular material, material properties, or construction techniques. In the present disclosure, the terms "chamber" and "bladder" are used interchangeably.

Figure 1B:
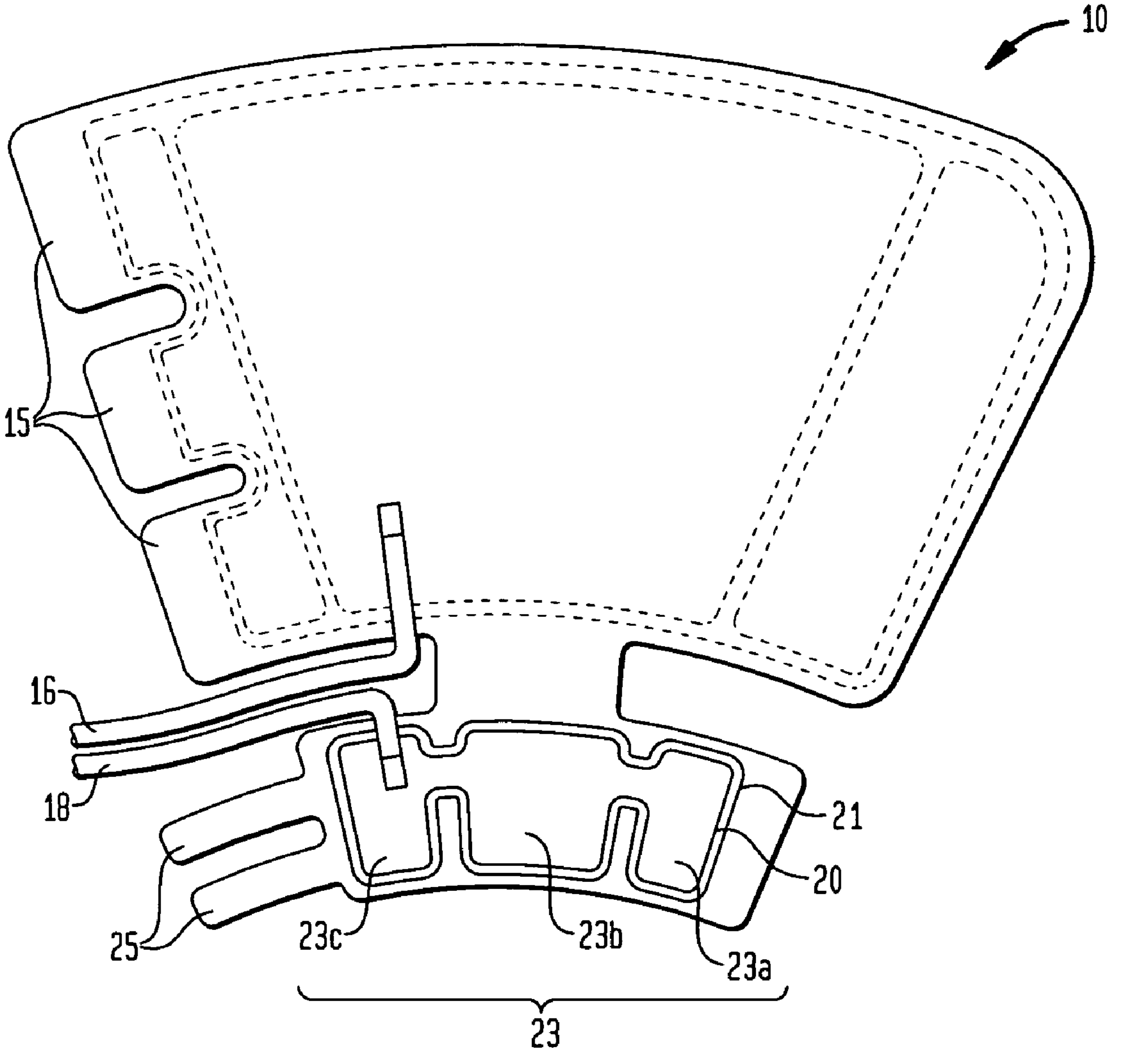

Referring now to FIGS. 1A and 1B, schematically depicted are plan views of a garment 10 according to an illustrative embodiment of a the present invention. More specifically, FIG. 1A is a plan view of garment 10 viewing the surface that contacts an individual's leg when garment 10 is in use ("the inner surface"), whereas FIG. 1B is a plan view of garment 10 viewing the surface opposite to the inner surface (this opposite surface also referred to herein as "the outer surface"). As depicted, the outer contour of garment 10 is configured so that garment 10 may be conformed about a patient's lower leg, extending from the ankle region and over the calf, with garment 10 being laterally wider towards the upper part of the leg (the proximal end) and tapering towards the lower part of the leg (the distal end).

In this embodiment, garment 10 comprises three sheets of plastic (e.g., PVC) material 11, 13, and 20, with sheet 13 and sheet 20 being disposed on the inner surface and outer surface, respectively, of sheet 11. Different materials and/or laminations of materials may be used for sheets 11, 13, and 20, such as neoprene, rubber, polymer, resin, and/or fabric materials. It is noted that throughout the various plan views, dashed lines denote structural features that are disposed beneath the upper sheet or layer of the surface being viewed and may be disposed on the opposite side of the backing sheet relative to the side from which the garment is being viewed. In some embodiments, inner sheet 13 and outer sheet 20 are more elastic than the backing sheet 11, which in some embodiments may be substantially inelastic. Backing and inner sheets 11 and 13 are high-frequency welded together at their peripheries and internally in a pattern 14 defining an airtight inflatable/deflatable bladder 12 and uninflatable, sealed chambers 17 and 19. Similarly, outer and backing sheets 20 and 11 are high-frequency welded together at their peripheries and internally in a pattern 21 defining an airtight inflatable bladder 23. As shown, the high frequency welds may be located internal to the periphery of garment 10 so that a hard edge consisting of the two material layers and weld join is avoided. The high frequency welds may be replaced by other available means for joining the materials, for example, ultrasonic welding, heat sealing, or adhesive bonding.

As depicted, bladder 23 comprises three fluidly/pneumatically coupled compartments or sub-chambers 23*a*, 23*b*, and 23*c*. In this embodiment, the sub-chambers are provided to facilitate chamber 23 wrapping about the ankle region. More specifically, as will be further understood below, this configuration provides for bladder 23 to be disposed about the ankle region while bladder 12 is disposed along and about the calf region, the latter providing for intermittent calf compression while the former elevates the patient's heel.

Although bladder 12 is depicted as a single chamber inflatable bladder as well as a chamber having no internal pattern, it will be understood that in alternative embodiments of the invention, bladder 12 may be implemented as a single chamber bladder having internal patterning (e.g., including baffling and/or seams provided by welding or otherwise joining materials 11 and 13 in a desired pattern) or as multi-chamber inflatable bladder, with each chamber possibly having internal patterns. Additionally, in the depicted embodiment, uninflatable sealed chambers 17 and 19 are provided so that the softer more elastic material 20 contacts the skin during use. In alternative embodiments, however, such uninflatable sealed chambers need not be provided. Also, in some embodiments, rather than bladder 23 being formed by joining (e.g., heat-welding) backing sheet 11 to sheet 20, a separately formed inflatable bladder may be attached (e.g., laminated) to backing sheet 11. Further, those skilled in the art will understand that alternative implementations of the invention may include additional material layers. For instance, in some embodiments, a breathable polyester foam layer may be laminated to the inner surface of garment 10 to, for example, increase comfort, reduce moisture/perspiration, and/or mitigate chafing, rash formation, and/or skin breakdown.

As shown in FIGS. 1A and 1B, one edge of garment 10 has tabs 15 having hook pile fabric on the inner surface thereof to engage loop pile fabric provided at least along a portion of the outside surface of garment 10 along the opposite edge, to secure the sleeve in place on the leg. Similarly, tabs or straps 25 each includes hook pile fabric on the inner surface thereof for engaging loop pile fabric provided on the outer surface of the distal section of garment 10 comprising bladder 23, to ensure that bladder 23 is maintained in position to provide proper and reliable heel elevation (e.g., despite patient movement). The hook and loop pile fabrics may be laminated (e.g., by adhesive or welding) to appropriate portions of garment 10. To secure the sleeve in place and/or to position/secure the elevation bladder, any of a variety of additional or alternative fastening mechanisms may be implemented, such as zippers, buttons, straps, laces, adhesive, etc. It is understood, however, that fastening mechanisms are not necessarily required for positioning and/or conforming the heel elevation bladder, and various embodiments of the present invention may be implemented which do not include fastening mechanisms and/or which provide for removably attachable fastening mechanisms (e.g., untethered straps with hook loop material provided at each end of one surface to engage loop material provided on the outer surface of the bladder). In some embodiments, for example, the heel elevation bladder may be configured or contoured such that it conforms about the ankle region upon inflation and securing of the garment about the patient's leg.

Compression bladder 12 and elevation bladder 23 are provided with conduits or tubes 16 and 18, respectively, for coupling to one or more fluid sources (not shown) used for inflating these chambers. A fluid (e.g., gas or liquid) source, for example, may be implemented as an air compressor/pump under control of a controller assembly that regulates air flow and/or pressure coupled to bladder 12 and bladder 23 via tubes 16 and 18. The controller assembly may include one or more feeder/supply valves and/or one or more exhaust valves pneumatically coupled to the bladders and to the compressor/pump, one or more pressure transducers to sense the pressure supplied to one or more bladders and/or the compressive pressure applied against the leg by the bladder(s), and a programmable processor-based control unit that monitors the pressure sensors and controls the valves to provide desired inflation/deflation timing and pressure for the compressive bladder(s) (e.g., bladder 12 in FIG. 1A) and, in some embodiments, also to control inflation of one or more heel elevation bladders (e.g., bladder 23 in FIG. 1A). The one or more feeder/supply valves and/or exhaust valves may be implemented as solenoid valves and may be configured in a valve manifold, which may further include one or more of the pressure transducers, to provide a desired pneumatic circuit configuration to provide for controlled inflation and/or deflation of garment chambers.

In operation, when the fluid source supplies compressed air to bladder 12 via tube 16, bladder 12 will inflate and apply sufficient pressure to the enclosed limb to augment venous return. An exhaust valve (e.g., in the pump manifold) may be opened, allowing the chamber to deflate via tube 16. The inflation and deflation rate, pressure, and duty cycle are appropriately controlled by the controller unit. In sequential compression garments, which include two or more separately-inflatable/deflatable and longitudinally disposed chambers, the controller unit also controls the relative inflation pressure and timing of the sequential chambers.

As indicated above, heel elevation bladder 23 may be pneumatically coupled via tube 18 (and, e.g., via a valve manifold) to the same controller unit and compressor/pump used for inflating/deflating bladder 12. In some implementations, heel elevation bladder 23 and bladder 12 may be coupled via respective tubes 18 and 16 to the fluid source via parallel and independent pneumatic circuits. In various implementations, heel elevation bladder 23 and bladder 12 may be alternately coupled via respective tubes 18 and 16 to the fluid source via a common pneumatic circuit path that is alternately connected to tubes 18 and 16 (e.g., using two valves synchronously switched 180 degrees out of phase). Accordingly, in this latter configuration, bladder 23 will be supplied with fluid pressure to inflate or maintain inflation during intervals that bladder 12 is deflated. In some such embodiments, bladder 12 may include a one-way valve (e.g., attached to sheet 20 where tube 18 couples thereto, or in series with and along tube 18) to prevent deflation during intervals that the fluid source is connected to tube 16. In some such embodiments, however, such a one-way valve need not be provided as the synchronously switched valve connected to tube 18 is closed during the interval that the fluid source is connected to tube 16, thus preventing deflation during such intervals.

It is understood that in embodiments of the present invention wherein two or more chambers are sequentially inflated to apply sequential compressive pressure to the patient, the pneumatic circuit and valve switch timing may be configured and controlled such that the fluid supply is alternately connected to each of the compressive bladders and the elevation bladder(s). Alternatively, in sequential compressive therapy implementations, two or more of the compression bladders may have independent pneumatic circuits coupled to the fluid source, and the heel elevation bladder(s) may be coupled to the fluid source via any one or more of these independent pneumatic circuits while each such pneumatic circuit is pneumatically disconnected from its associated compressive bladder (e.g., while that bladder is in a deflation state). In this way, independent pneumatic circuits supplying the compressive bladders may be multiplexed to supply one or more heel elevation bladders.

In alternative embodiments, bladder 23 may be fluidly coupled via tube 18 to a separate fluid source (e.g., compressor) and controller. As noted above, in some embodiments, heel elevation bladder 23 may be inflated via a one-way valve, which, for example, may be attached directly bladder 23 or pneumatically in series with tube 18.

As will be understood, in alternative embodiments, heel elevation bladder 23 need not be continuously or intermittently supplied by a fluid source during use. For instance, in some embodiments, heel elevation bladder 23 may be initially inflated using any inflation source, such as the pump/compressor used for intermittent inflation of bladder 12, a manual pump, a compressed air cylinder coupled to a regulator, etc. After inflation, the inflation source may be disconnected from heel elevation bladder 23, which is provided with a sealable valve or a one way valve (e.g., affixed to bladder 23 or coupled thereto, e.g., via tube 18) to allow for retaining the fluid (e.g., air) within bladder 23 after the inflation source is disconnected and during patient use of garment 10. In various embodiments, however, it may be advantageous for heel elevation bladder 23 to remain coupled to a fluid source to ensure that sufficient heel elevation is maintained during patient use of garment 10 for compressive therapy (which may be a prolonged time period), despite possible leakage from bladder 23.

In some embodiments, heel elevation bladder 23 may be deflated (e.g., after use, or when the patient wishes to ambulate without removing the garment). Deflation of heel elevation bladder 23 may be provided in various ways depending on the particular implementation; for example, deflation may be provided by any combination of one or more of the following: via an exhaust valve in the pump manifold, via bladder leakage, via an exhaust valve coupled to conduit 18, and/or via a separate releasable plug/valve (not shown) provided on the bladder 23.

Figure 2:
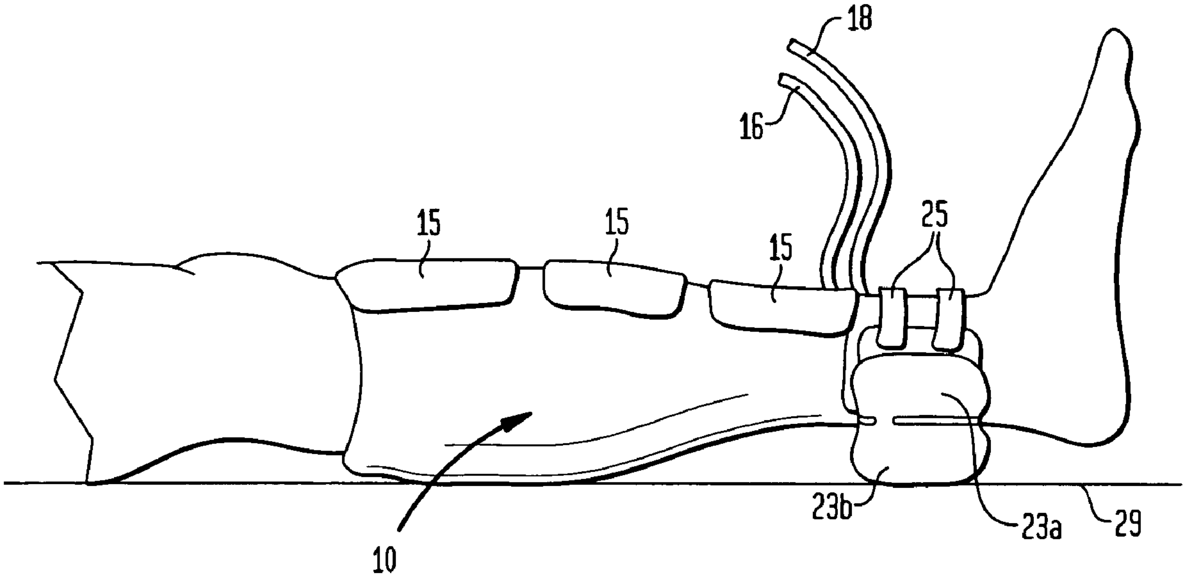
FIG. 2 schematically depicts a side view of the compression garment of FIGS. 1A and 1B attached to an individual's leg, in accordance with an embodiment of the present invention.

FIG. 2 schematically depicts a side view of garment 10 attached to a patient's leg, with the heel elevation bladder 23 inflated, in accordance with an embodiment of the present invention. As embodied, the maximum displacement between the outer and inner surfaces of the bladder 23 (i.e., when the bladder is fully inflated) is sufficient to elevate the patients heel such that the heel is spaced away from an underlying surface 29 (e.g., a bed), which surface the patient's heel would rest upon but for the elevation provided by heel elevation device 10. By way of example, such maximum displacement may be about two to four inches. It is understood, however, that even if the patient's heel or foot is cantilevered off the edge of an underlying surface (e.g., bed), heel elevation device 10 is still useful for preventing, for example, possible abrasions or shear, possible digging of the heels in the bed, heel pressure in the event the patient moves such that the foot or leg is no longer cantilevered, as well as for reducing or preventing pressure on the Achilles tendon and/or reducing or preventing other concentrated pressure that may affect circulation. As depicted, in this embodiment heel elevation bladder 23 is positioned at or near the ankle region, with bladder compartment 23*b* supporting the rear of the ankle and bladder compartment 23*a* disposed at the side of the ankle. Bladder 23 is inflated to a desired level of inflation (e.g., inflation pressure) to provide the desired heel elevation, cushioning/firmness, and/or stability. As will be appreciated, the elevation height may be adjustable, based on the volume (and hence pressure) of air pumped into the bladder.

In this illustrative embodiment, the inelasticity (and semi-rigidity in some implementations) of backing 11 may also prevent or mitigate excessive inward pressure against the back of the leg as the bladder 23 is inflated, which pressure could adversely affect circulation or control of compressive pressure, particularly in view of straps 25 securing the ankle support portion about the ankle. It is understood, however, that such prevention or mitigation of inward pressure by the heel elevation bladder is not a necessary feature for implementing embodiments of the present invention. In some embodiments, at least a certain degree of inward inflation by the elevation bladder is advantageous for distributing the pressure over the back of the leg, conforming to the leg, and/or providing stable support (e.g., lateral support) for elevating the heel and reducing heel pressure.

As noted above, backing sheet 11 may be substantially inelastic; for example, backing sheet 11 may be sufficiently or substantially inelastic such that it does not substantially deform when garment 10 is attached in position to a patient's leg for compressive therapy and bladders 12 and 23 are inflated. As such, bladder 12 will primarily or predominantly expand against the patient's leg as it expands upon inflation, thereby predominantly and efficiently translating and coupling the inflation pressure as compressive pressure against the patient's leg. Also as such, with bladder 23 disposed on the outer surface of backing sheet 11 and backing sheet 11 being substantially inelastic, bladder 23 will primarily or predominantly expand in a posterior direction, outwardly and away from the patient's leg as it expands upon inflation, thereby avoiding unintended leg (e.g., ankle) compression that may adversely affect compressive therapy and/or adversely affect the patient (e.g., by decreasing blood flow).

It may be appreciated, however, that in some embodiments, such as wherein the heel elevation bladder segment of garment 10 is not configured to necessarily encircle the ankle region, the portion of backing sheet 11 that is disposed against the elevation bladder may be elastic (e.g., having the same elasticity as the outer facing elevation bladder material), as inflation of the heel elevation bladder will not necessarily apply compressive pressure against the patient's leg without the heel elevation bladder portion of garment 10 being secured about the leg (e.g., ankle). In some embodiments, such a configuration may alternatively be provided by separately forming (i) the proximal portion of the garment comprising the upper compression bladder (e.g., corresponding to bladder 12 in FIG. 1A) by radio-frequency welding an elastic sheet and a substantially inelastic sheet, and (ii) the distal portion of the garment comprising the heel elevation bladder (e.g., similar to bladder 23 in FIG. 1A, but without an inelastic sheet) by radio-frequency welding two sheets of elastic material. Then, the proximal portion and distal portion may be welded together at their respective distal and proximal edges to form the completed garment.

Moreover, it may be understood that in various alternative embodiments, heel elevation bladder may be implemented to function for both elevating the heel and applying intermittent compressive pressure (e.g., as part of a sequential compression device). For instance, in some such embodiments, such as a garment constructed similarly to that described in the previous paragraph, the heel elevation bladder portion of the garment may be inflated to a baseline pressure sufficient to elevate the heel at a desired level, and then secured (e.g., using straps or extensions similar to straps 25 in FIGS. 1A and 1B) about the patient's lower leg (e.g., ankle region) such that it does not apply excessive compressive pressure against the patient's leg at the baseline pressure. In operation, the heel elevation bladder may be controllably and intermittently (e.g., periodically, sequentially with one or more other bladders longitudinally disposed along the leg) inflated to a desired pressure above the baseline pressure to intermittently apply compressive pressure against the ankle region to assist venous return, with the heel elevation bladder being controllably deflated back to the baseline pressure for intervals between inflation cycles.

Figure 3:
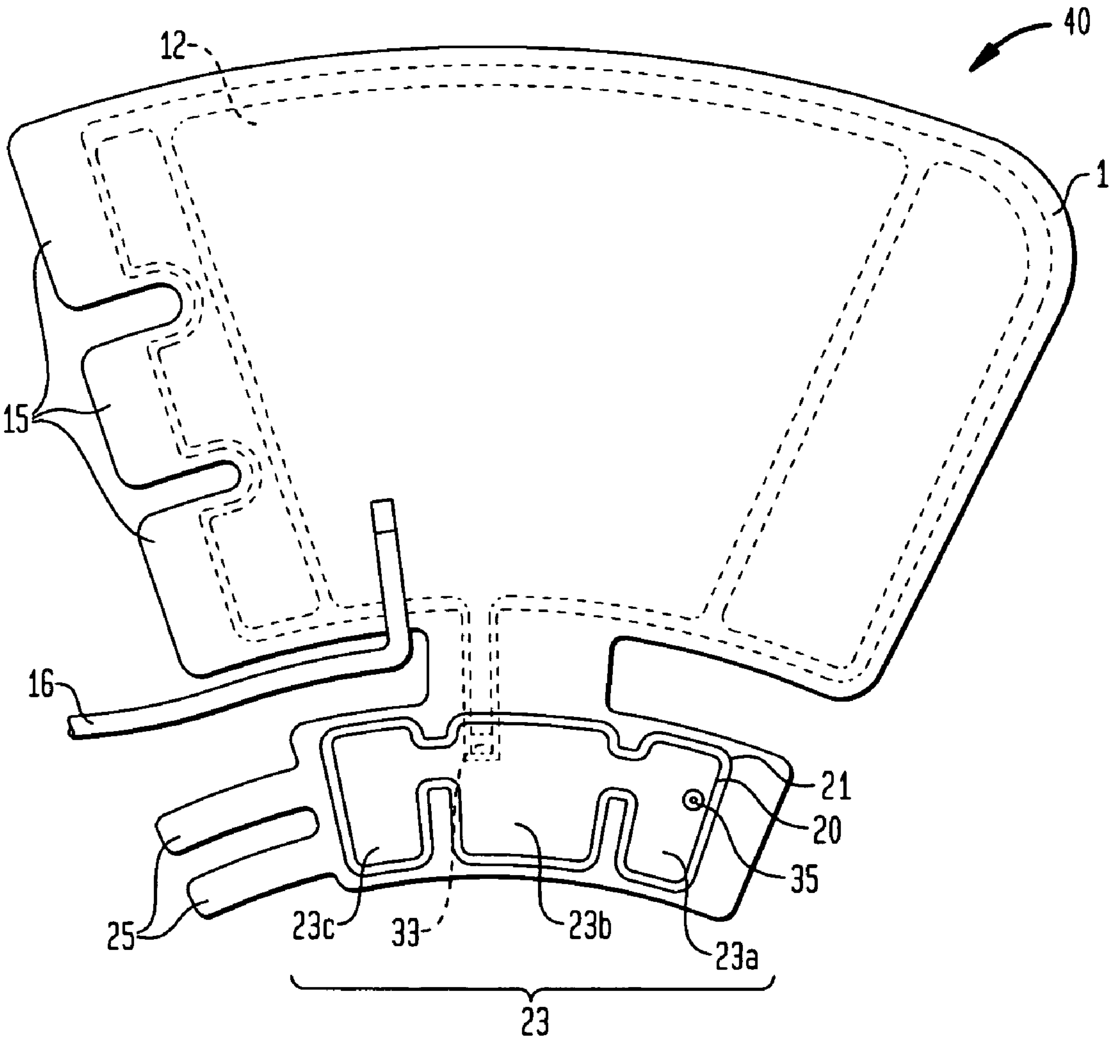
FIG. 3 schematically depicts a plan view of a compression garment, in accordance with another embodiment of the present invention.

Referring now to FIG. 3, schematically depicted is a plan view of the outer surface of a garment 40 according to an alternative embodiment of the present invention. As shown, garment 40 is similar in construction to garment 10 depicted in FIGS. 1A and 1B. In this embodiment, however, bladder 23 is not inflated via a separate tube, but rather is pneumatically coupled to bladder 12 via lumen or tube 31 and a one-way valve 33, which valve passes through or traverses backing sheet 11. Accordingly, upon controlled inflation of compressive bladder 12 via tube 16, bladder 23 will be inflated and maintained in an inflated state. Bladder 23 may be include a pressure relief and/or exhaust valve 35 disposed through sheet 20 to ensure bladder 23 is not over-inflated and/or to deflate bladder 23 when desired. It will be understood that while in this embodiment lumen 31 is disposed on the inner surface of the garment and valve 33 traverses sheet 11 in the region of bladder 23, in an alternative embodiment valve 33 may traverse sheet 11 within the region of bladder 12 with lumen 31 disposed on the outer surface of garment 40.

Figure 4:
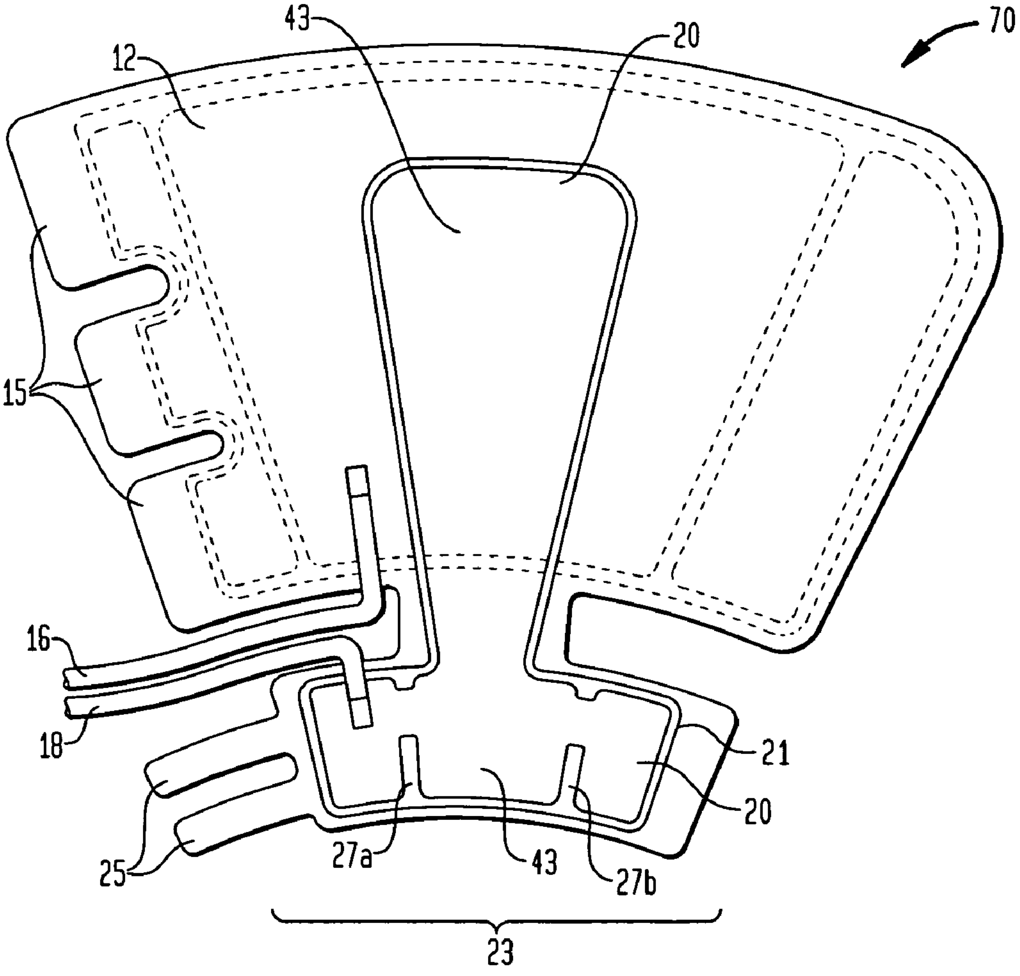
FIG. 4 schematically depicts a plan view of a compression garment, in accordance with another embodiment of the present invention.

FIG. 4 schematically depicts a plan view of the outer surface of a garment 70, in accordance with another illustrative embodiment of the present invention. As shown, garment 70 is similar in construction to garment 10; however, heel elevation bladder 43 is generally T-shaped, with a portion extending longitudinally along the outer surface of backing sheet 11 such that this longitudinal portion is disposed opposite to bladder 12 over a region that extends from approximately the mid-calf to the upper ankle when the garment is attached to a patient's leg. As shown, bladder 43 also includes a distal portion (similar to bladder 23) that extends laterally and is segmented by seams 27*a* and 27*b* and supports the ankle region when in use. Tube 18 is coupled into bladder 43 to provide for inflation thereof. In alternative implementations, tube 18 may be eliminated, and bladder 43 may be pneumatically coupled to bladder 12, similar to the pneumatic coupling of compressive pressure and heel elevation bladders in the embodiment depicted in FIG. 3.

Figure 5:
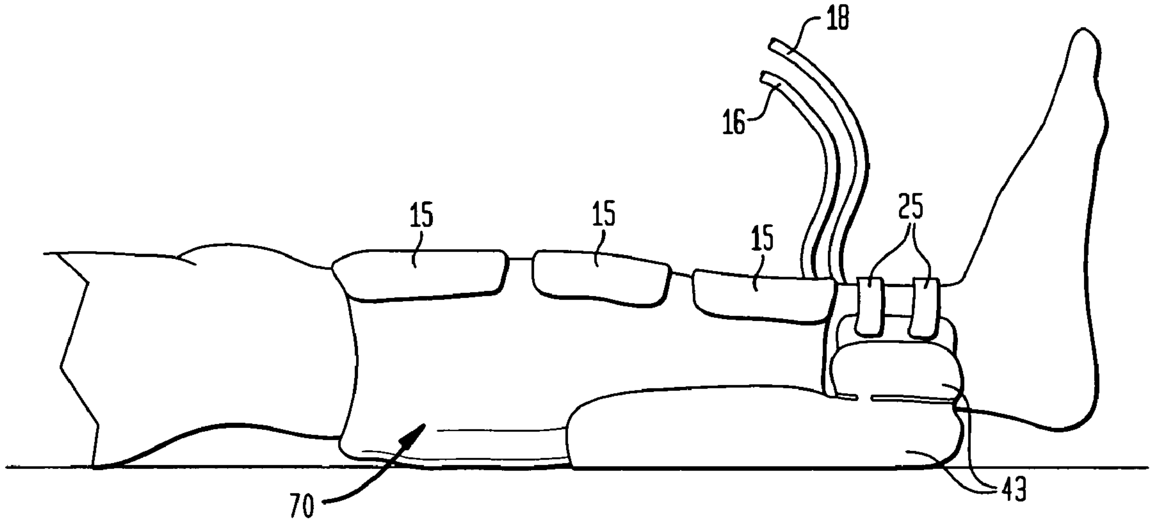
FIG. 5 schematically a side view of the compression garment of FIG. 4 attached to an individual's leg, in accordance with an embodiment of the present invention.

FIG. 5 schematically depicts a side view of garment 70 attached to a patient's leg, with the heel elevation bladder 43 inflated, in accordance with an embodiment of the present invention. As may be understood from this side view, in some embodiments the cross sectional profile in the sagittal plane may have a generally trapezoidal, tapered shape that generally complements the contour of the adjacent rear leg portion such that the outer surface (posterior surface) of bladder 43 is generally parallel to the shin. It may also be understood that in some embodiments, more than one separately inflatable posterior bladder may be provided along the length (longitudinally) between the proximal and distal ends. The cross sectional elevation profile in the sagittal plane (i.e., elevation along the longitudinal direction) may thus be adjusted by separately adjusting the pressure of each posterior bladder provided. Alternatively, or additionally, an elevation bladder (e.g. bladder 43) may be apportioned into multiple sections that are commonly inflated, but have different shapes or contain different volumes of fluid when the bladder is inflated. For instance, bladder 43 may be adapted to include multiple longitudinal and/or lateral sections by, for example, separating the sections with baffles or seams that may be formed by heat sealing or welding the outer surface of the bladder (i.e., sheet 20) to the inner surface (i.e., sheet 11) along most of the extent dividing adjacent sections, but leaving an opening (lumen) between adjacent sections such that fluid (e.g., air) can flow therethrough (as will be understood, a section of tubing or foam or other fluid-permeable membrane may be positioned within the opening(s) to prevent kinking from impeding airflow). Accordingly, upon inflation, each of the sections will be filled, but the shape/profile of each section may be determined by the baffle/seam configuration/shape and the fluid containing volume of each section separated by the baffles.

Figure 6:
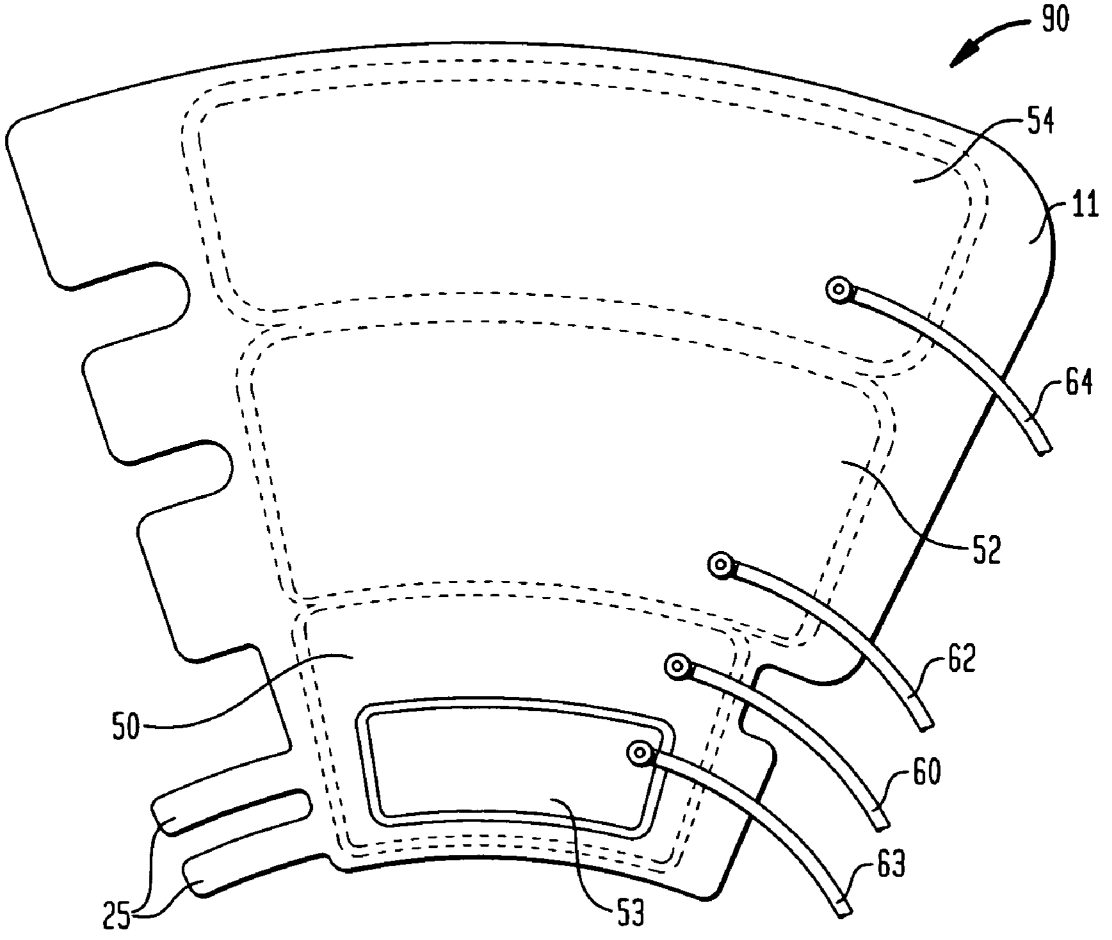
FIG. 6 schematically depicts a plan view of a compression garment, in accordance with an embodiment of the present invention.

FIG. 6 schematically depicts a plan view of the outer surface of a garment 90, in accordance with another illustrative embodiment of the present invention. As shown, garment 90 is generally similar in construction to garment 10; however, rather than providing a heel elevation bladder that is disposed distally relative to the compression chamber(s), in this embodiment the heel elevation bladder is oppositely opposed to a compression chamber. More specifically, as shown, in this embodiment garment 90 includes three pneumatically separate chambers, namely, upper-calf bladder 54 fluidly coupled to tube 64 for coupling to a fluid source, lower-calf bladder 52 fluidly coupled to tube 64 for coupling to a fluid source, and lower-leg/ankle bladder 50 fluidly coupled to tube 60 for coupling to a fluid source. Additionally, as shown, in this embodiment heel elevation bladder 53 is disposed on the outer surface of backing sheet 11 opposite to lower-leg/ankle bladder 50, and is fluidly coupled to tube 63 to provide for inflation thereof. In various embodiments, bladder 53 may include baffles/seams (not shown) to, for example, facilitate generally conforming bladder 53 about the ankle region when in use. In alternative implementations, tube 63 may be eliminated, and bladder 53 may be pneumatically coupled to bladder 50 (e.g., using a one-way valve through intervening sheet 11), similar to the pneumatic coupling of compressive pressure and heel elevation bladders in the embodiment depicted in FIG. 3. The pneumatically separate chambers 50, 52, 54 may be controllably inflated and deflated to provide for sequential compression to augment venous return, as understood by those skilled in the art. In an alternative variation, appropriate orifices or pressure relief valves may be substituted for inflation tubes 62 and 64 (and associated ports/couplings into bladders 52 and 54), and bladders 50, 52, and 54 may be pneumatically coupled in series by restrictors such that these chambers are sequentially inflated upon inflation via tube 60, in accordance with compression devices described in US Patent Publication No. US 2005/0070828 A1 to Hampson et al.

Figure 7:
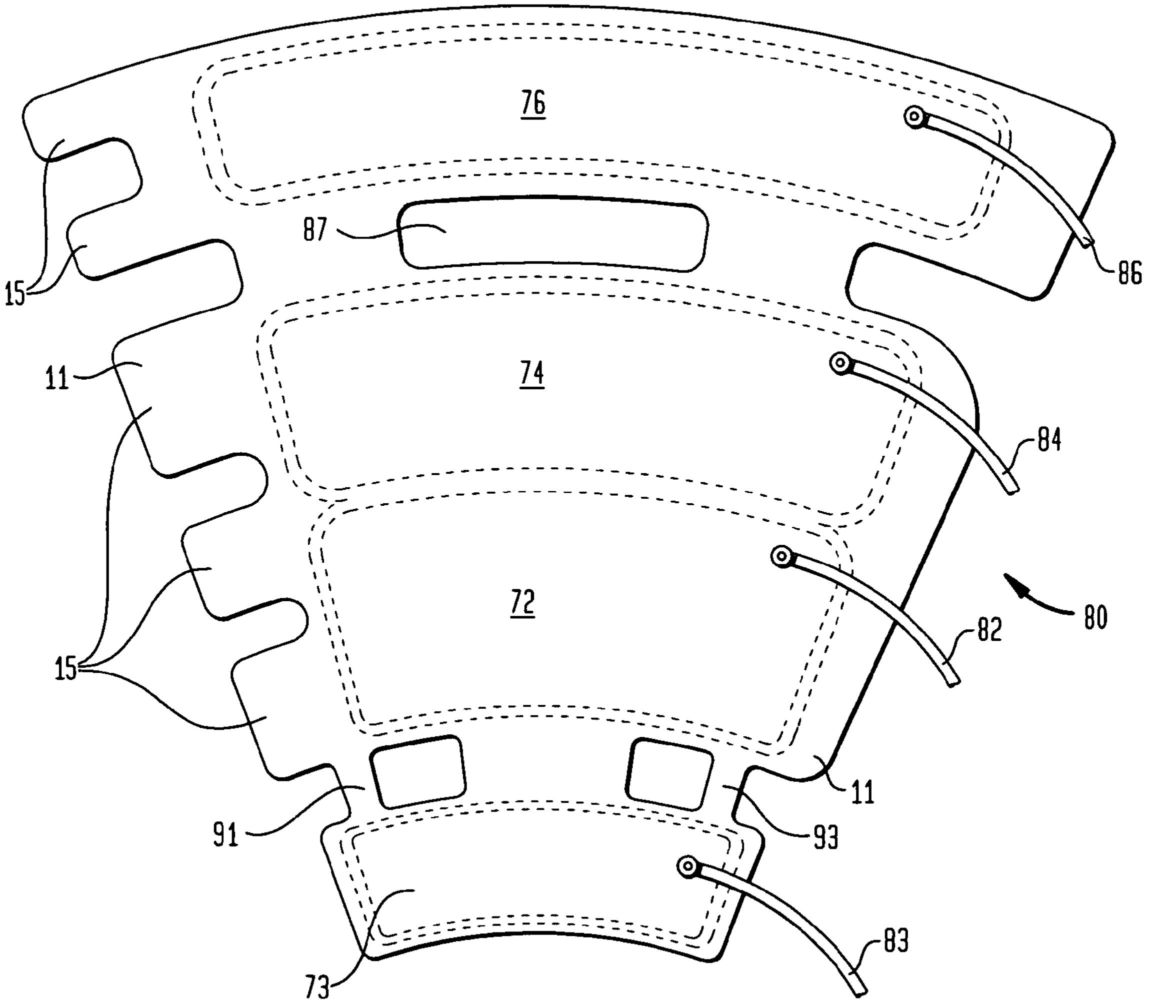
FIG. 7 schematically depicts a plan view of a compression garment, in accordance with an embodiment of the present invention.

FIG. 7 schematically depicts a plan view of the outer surface of a garment 80, in accordance with another illustrative embodiment of the present invention. As shown, garment 80 is generally similar in construction to garment 90; however, garment 80 provides a thigh compression chamber, and also provides a heel elevation bladder 73 that is disposed distally relative (rather than partially or entirely opposite) to the compression chamber(s). More specifically, garment 90 includes three pneumatically independent chambers, namely, thigh-bladder 76 fluidly coupled to a tube 86 for coupling to a fluid source, upper-calf bladder 74 fluidly coupled to tube 84 for coupling to a fluid source, and lower-calf bladder 72 fluidly coupled to tube 82 for coupling to a fluid source. Additionally, as shown, in this embodiment heel elevation bladder 73 is disposed distally with respect to the compression chambers, and is fluidly coupled to tube 83 to provide for inflation thereof. Backing sheet 11 includes an opening 87 to accommodate the knee when affixing the garment about a patient's leg. Segments 91 and 93 mechanically couple the lateral ends of the elevation bladder portion to the lateral ends of the compression bladder portion of garment 80, thus facilitating conformance of the heel elevation bladder about the ankle region (e.g., without additional straps wrapping around the ankle, such as straps 25 in the embodiment of FIGS. 1A and 1B. In this embodiment, segments 91 and 93 are each an integral part of sheet 11, but in various alternative implementations may be separate/discrete members attached (e.g., by radio-frequency welding) to sheet 11. In various alternative embodiments, segments 91 and 93 may be the only mechanical coupling between the elevation bladder portion and the compression bladder portion of garment 80.

The present invention has been illustrated and described with respect to specific embodiments thereof, which embodiments are merely illustrative of the principles of the invention and are not intended to be exclusive or otherwise limiting embodiments. For instance, while in the foregoing embodiments, compressive therapy garments include integrally attached or formed bladders that are inflatable and deflatable, it will be understood that in alternative implementations within the purview of the present invention, compressive therapy garments may alternately or additionally include integrally formed or attached (e.g., by adhesive, radio-frequency welding, etc.) heel elevation members that are not configured for inflation and/or deflation. For instance, such heel elevation members may be implemented using any of a variety of preformed and/or prefilled cushioning materials such as foam cushions and/or air, gel, or other fluid filled uninflatable/undeflatable cushions, provided such heel elevation members provide sufficient elevation for mitigating and/or eliminating heel pressure. It is noted, however, that inflatable/deflatable bladders are well suited for providing adjustability of elevation and cushioning/firmness, as well as for evenly distributing/redistributing pressure and conforming to the patients leg, even under dynamic load conditions (e.g., resulting from patient movements that may change the load conditions). As yet a further illustrative example of variations within the purview of the present invention, more than one separately inflatable bladder may be provided in the posterior direction to allow variable height adjustment and cushioning pressure by selectively filling one or more bladders. Also, for example, while the foregoing embodiments illustrate heel elevation in connection with a calf and/or thigh compression chambers, alternative embodiments of the present invention may additionally or alternatively include a foot compression chamber together with a heel elevation bladder. Further, while particular shapes, sizes, and materials have been described for purposes of illustration, it will be recognized that any of a variety of shape or size can be used, and the materials described are not exclusive but merely illustrative. Also, as noted hereinabove, while the bladder shown is inflated with air, it will be appreciated that any other fluid or medium such as liquid or gel can be used. Moreover, as also noted, it will be understood that bladders may be configured to have multiple pneumatically independent and/or pneumatically coupled bladder sections, and may also configured to have various contours or lobulations.

Accordingly, although the above description of illustrative embodiments of the present invention, as well as various illustrative modifications and features thereof, provides many specificities, these enabling details should not be construed as limiting the scope of the invention, and it will be readily understood by those persons skilled in the art that the present invention is susceptible to many modifications, adaptations, variations, omissions, additions, and equivalent implementations without departing from this scope and without diminishing its attendant advantages. It is further noted that the terms and expressions have been used as terms of description and not terms of limitation. There is no intention to use the terms or expressions to exclude any equivalents of features shown and described or portions thereof. Additionally, the present invention may be practiced without necessarily providing one or more of the advantages described herein and/or that may be realized in some embodiments thereof. It is therefore intended that the present invention is not limited to the disclosed embodiments but should be defined in accordance with the claims that follow.

What is claimed is:

1. A compression garment, comprising:

a backing member configured to be disposed about at least a lower leg portion of an individual between the calf and heel region, said backing member having an inner surface to be disposed facing the leg, and having an opposite outer surface;

at least one compression bladder disposed on the inner surface of said backing member and configured for being operable to intermittently apply sufficient pressure to at least a portion of the calf of the lower leg to sufficiently augment venous return flow in the lower leg to provide for compressive therapy; and an elevation member including an inflatable-deflatable bladder, the elevation member being mechanically coupled to said backing member and configured such that when the backing member is disposed about at least the lower leg portion of the individual for the at least one compression bladder to apply sufficient pressure to at least a portion of the calf of the lower leg to sufficiently augment venous return flow, the elevation member is disposed near the heel and is capable of elevating the heel from an underlying surface in the event that the lower leg portion is extended above the underlying surface.

2. The compression garment according to claim 1, wherein the inflatable bladder is pneumatically independent from each of said at least one compression bladder.

3. The compression garment according to claim 1, wherein the inflatable bladder is pneumatically coupled to at least one of said at least one compression bladder.

4. The compression garment according to claim 1, wherein the inflatable bladder is disposed on the outer surface of said backing member.

5. The compression garment according to claim 4, wherein the inflatable bladder is disposed distally to each of said at least one compression bladder.

6. The compression garment according to claim 4, wherein the inflatable bladder is disposed at least partially on the opposite side of the backing member from at least one of said at least one compression bladder.

7. The compression garment according to claim 4, wherein the inflatable bladder comprises a portion that extends longitudinally along the outer surface of at least a portion of said backing member that is disposed between the lower calf and to the upper ankle when the garment is disposed about the individual's leg.

8. The compression garment according to claim 7, wherein said inflatable bladder includes a distal portion that extends laterally and is disposed adjacent the individual's ankle when the garment is disposed about the individual's leg.

9. The compression garment according to claim 8, wherein the distal portion of the inflatable bladder includes opposing lateral portions disposed adjacent to opposite lateral sides of the lower leg relative to the saggital plane when the garment is disposed about the individual's leg.

10. The compression garment according to claim 1, wherein the inflatable bladder is apportioned into a plurality of pneumatically coupled regions separated by at least one baffle or seam.

11. The compression garment according to claim 1, wherein the inflatable bladder is capable of being selectively and repeatedly inflated and deflated.

12. A compression garment, comprising:

at least one compression chamber configured for being operable to intermittently apply sufficient pressure to at least a portion of an individual's limb to sufficiently augment venous return flow in the individual's limb to provide for compressive therapy, said at least one compression chamber capable of being coupled to a fluid source and configured to inflate and apply pressure against at least a portion of the individual's limb in response to receiving a fluid input from the fluid source;

a backing member having an inner surface that is disposed toward the individual's limb upon application of the garment, said backing member having an outer surface opposite said inner surface, and wherein the inflatable bladder is disposed on the outer surface of said backing member, and the at least one compression chamber is disc used on the inner surface of said backing member; and at least one inflatable-deflatable elevation chamber configured to elevate at least a portion of the individual's limb when inflated.

13. The compression garment according to claim 12, wherein the individual's limb is a leg and the at least one inflatable elevation chamber is configured to elevate the individual's heel.

14. The compression garment according to claim 12, wherein the inflatable elevation chamber is pneumatically independent from each of said at least one compression chamber.

15. The compression garment according to claim 12, wherein the inflatable elevation chamber is pneumatically coupled to at least one of said at least one compression chamber such that the inflatable elevation chamber is inflatable via the pneumatic coupling to said at least one compression chamber.

16. The compression garment according to claim 12, wherein the inflatable elevation chamber is capable of being selectively and repeatedly inflated and deflated.

* * * * *